(12) United States Patent
Nishio et al.

(10) Patent No.: US 7,976,690 B2
(45) Date of Patent: Jul. 12, 2011

(54) METHOD FOR PRODUCTION OF RESPONSIVE GLASS MEMBRANE FOR ION ELECTRODE, RESPONSIVE GLASS MEMBRANE FOR ION ELECTRODE, AND ION ELECTRODE

(75) Inventors: Yuji Nishio, Kyoto (JP); Yasukazu Iwamoto, Kyoto (JP); Tadanori Hashimoto, Tsu (JP)

(73) Assignees: HORIBA, Ltd., Kyoto-shi (JP); Mie University, Tsu-shi (JP)

( * ) Notice: Subject to any disclaimer, the term of this patent is extended or adjusted under 35 U.S.C. 154(b) by 229 days.

(21) Appl. No.: 12/518,630

(22) PCT Filed: Dec. 11, 2007

(86) PCT No.: PCT/JP2007/073830
§ 371 (c)(1),
(2), (4) Date: Jun. 10, 2009

(87) PCT Pub. No.: WO2008/072612
PCT Pub. Date: Jun. 19, 2008

(65) Prior Publication Data
US 2010/0025235 A1  Feb. 4, 2010

(30) Foreign Application Priority Data
Dec. 11, 2006  (JP) .................................. 2006-333637

(51) Int. Cl.
*G01N 27/333* (2006.01)
*G01N 27/36* (2006.01)
*C03B 19/09* (2006.01)
*C03B 32/02* (2006.01)
*B32B 17/06* (2006.01)

(52) U.S. Cl. ................. 204/420; 65/47; 65/48; 428/432
(58) Field of Classification Search ................. 204/420; 65/47, 48; 428/432
See application file for complete search history.

(56) References Cited

U.S. PATENT DOCUMENTS
2008/0206547 A1* 8/2008 Nishio et al. ............... 428/319.1
2008/0207428 A1* 8/2008 Nishio et al. ................... 501/49

FOREIGN PATENT DOCUMENTS
| JP | 2000-143293 | 5/2000 |
| JP | 2001-080939 | 3/2001 |
| JP | 2003-201145 | 7/2003 |
| JP | 2006-017627 | 1/2006 |
| WO | 2005-030664 | 4/2005 |

OTHER PUBLICATIONS
ISA/Japanese Patent Office, International Search Report of PCT/JP2007/073830, Jan. 22, 2008, 4 pages, Japan.

* cited by examiner

*Primary Examiner* — Bruce F Bell
(74) *Attorney, Agent, or Firm* — Alleman Hall McCoy Russell & Tuttle LLP

(57) ABSTRACT

Disclosed is a sensitive glass film for a pH electrode, which is not deteriorated in its glass strength or pH-measuring function, which is hardly stained, and from which any stain can be removed easily. Also disclosed is a pH electrode having the sensitive glass film. A microparticle comprising rutile-type or brookite-type titanium dioxide or a microparticle comprising amorphous titanium dioxide is adhered directly on the glass film surface of a sensitive glass film for a pH electrode.

8 Claims, 4 Drawing Sheets

METHOD FOR PRODUCTION OF RESPONSIVE GLASS MEMBRANE FOR ION ELECTRODE, RESPONSIVE GLASS MEMBRANE FOR ION ELECTRODE, AND ION ELECTRODE

FIELD OF THE INVENTION

The present invention relates to a responsive glass membrane for a pH electrode, which is not deteriorated in its glass strength or pH-measuring function, which is hardly stained, and on which any stain can be removed easily, and also to an ion electrode providing such a membrane.

BACKGROUND ART

Crystal type of titanium dioxide ($TiO_2$, titania) includes rutile type and anatase type, and it is known conventionally that anatase-type crystalline titanium dioxide doped with nitrogen develops a photocatalytic function in response to visible light (Nonpatent document 1). The photocatalytic function includes a powerful oxidation action and a superhydrophilic action. For example, the oxidation action is utilized to coat a wall and a floor of an operation room in a hospital with titanium dioxide to provide the sterilization treatment. The superhydrophilic action is utilized to coat a side view mirror of a car and a road mirror with titanium dioxide to provide a glass antifog treatment capable of self-cleaning if it rains, and also is applied to prevent an external wall of a building and a tent sheet from being stained.

Then, a stain on a responsive glass membrane of a pH electrode causes an asymmetric potential which causes an error in the measurement value. In order to maintain an accuracy of the measurement, it is necessary to clean the responsive glass membrane thoroughly using a detergent and the like to remove the stain stuck thereto each time the measurement is performed.

Nonpatent document 1: Kazuhito Hashimoto, et al., Hikari shokubai, Kiso/Zairyo Kaihatsu/Oyo (Photocatalysis, Fundaments/Material Development/Application), issued on Jun. 22, 2004 published by NTS Inc.

DISCLOSURE OF THE INVENTION

Problems to be Solved by the Invention

Therefore, it is contemplated that, if the photocatalytic function of titanium dioxide can be utilized on the responsive glass membrane, the cleaning can be easily performed.

However, conventionally, coating a glass with titanium dioxide has been done by the method in which titanium dioxide is dispersed into an adhesive solution and then it is applied on the glass surface (Japanese Unexamined Patent Publication No. 2002-14078). However, an impurity such as the adhesive stuck on the surface makes the extremely thin glass, like the responsive glass membrane for the pH electrode, fragile. Further, the adhesive and the like covering the surface of the responsive glass membrane for the pH electrode inhibit the pH responsiveness.

When anatase-type titanium dioxide, which has the powerful photocatalytic function as described above, is applied on the surface of the responsive glass membrane for the pH electrode, the superhydrophilic action generates a hydrophilic radical that causes a potential variation, and the oxidation action affects the test solution to be measured such that it decomposes and the ingredients thereof are changed. These may interfere with the pH measurement.

The present invention is thus intended to provide a responsive glass membrane for an ion electrode such as a pH electrode, which is not deteriorated in its glass strength or ion measurement function such as pH measurement, which is hardly stained, and from which any stain can be removed easily, and to provide an ion electrode providing such a membrane.

Means Adapted to Solve the Problems

Specifically, the responsive glass membrane for the ion electrode according to the present invention is characterized by including a microparticle comprising rutile-type or brookite-type titanium dioxide or a microparticle comprising amorphous titanium dioxide sticking directly to the glass membrane surface.

In the present invention, a microparticle sticking directly to a glass membrane surface implies nothing is interposed between the glass membrane and the microparticle, and also the adhesive does not exist.

A photocatalytic function of the rutile-type titanium dioxide is lower than that of anatase-type titanium dioxide, and is not induced by the light intensity of ultraviolet irradiation at the level of inducing a photocatalytic function of the anatase titanium dioxide. The rutile-type titanium dioxide placed in natural light or in normal indoor lighting generates a slightly hydrophilic radical, which has a minimal effect on the ion measurement such as the pH measurement, while not developing an oxidation action.

In addition, it has been recently reported that the amorphous titanium dioxide also exhibits the photocatalytic function (Optical Alliance, March 2004 issue, 13 to 17). The photocatalytic function thereof, however, is extremely low.

The ultraviolet irradiation to the rutile-type titanium dioxide and the amorphous titanium dioxide, however, induces a greater photocatalytic function, so that an organic substance is decomposed due to the oxidation action, and the superhydrophilic action increases a hydrophilic radical that makes a stain easy to remove.

Therefore, when measuring the ion concentration such as pH under natural light or normal indoor lighting, the responsive glass membrane for the ion electrode according to the present invention generates a slight hydrophilic radical that increases the hydrophilicity, and thus is hardly stained. Also, the increased hydrophilicity suspends a stain, so that the stain can be removed to a certain extent only by water without using any surface active agents at the time of cleaning. In addition, the ultraviolet irradiation induces the greater photocatalytic function, so that a so-called self-cleaning function can be fulfilled in which an organic substance stuck to the responsive glass membrane is decomposed by the oxidation action, and the superhydrophilic action makes the stain stuck to the responsive glass membrane easy to remove. The responsive glass membrane thus can be easily kept clean, thereby enabling the measurement to be performed constantly with a high accuracy. As a light source of the ultraviolet irradiation, it is possible to use, for example, an LED, a hydrogen lamp, a xenon discharge tube, a mercury lamp, a ruby laser, a YAG laser, an excimer laser, or a dye laser. Moreover, the responsive glass membrane for the pH electrode may be heated to about 400° C. to 500° C. at the time of cleaning.

Further, the responsive glass membrane for the ion electrode according to the present invention does not include anything interposing between the glass membrane surface and the microparticle comprising the rutile-type titanium dioxide or the microparticle comprising the amorphous titanium dioxide. Since the microparticle comprising the rutile-type titanium dioxide or the microparticle comprising the amorphous titanium dioxide stick directly to the glass membrane surface, the glass membrane made of extremely thin glass is not deteriorated in its strength.

Furthermore, the rutile-type or brookite-type titanium dioxide and the amorphous titanium dioxide used in the present invention take the form of a microparticle, so that the surface areas thereof can be larger, thereby enabling the stain-resistance function and the self-cleaning function to be developed more effectively.

The ion electrode provided with such a responsive glass membrane for the ion electrode according to the present invention is another object of the present invention. Specifically, the ion electrode according to the present invention is characterized by including a responsive glass membrane including the microparticle comprising the rutile-type or brookite-type titanium dioxide or the microparticle comprising the amorphous titanium dioxide sticking directly to the surface thereof.

The responsive glass membrane for the ion electrode according to the present invention is characterized by being manufactured by way of a membrane molding process to melt a glass raw material and mold it into a glass membrane having a predetermined shape; and a sticking process to stick titanium dioxide to a surface of the glass membrane kept molten at intervals. Such a production method is another object of the present invention.

More specifically, it is preferable to stick the microparticle comprising titanium dioxide to the surface of the glass membrane kept molten during the aforementioned sticking process.

Further, it is contemplated that the method further includes a suspending process to suspend the microparticle within gas, wherein the microparticle suspended within the gas sticks to the surface of the glass membrane in the sticking process so as to directly stick the microparticle comprising titanium dioxide to the glass membrane surface.

Furthermore, the responsive glass membrane for the ion electrode according to the present invention can be produced by the following processes: a melting process to melt a tip portion of a glass tube; a dipping and sticking process to dip the tip portion molten during the melting process into a mounted aggregation of fine powder of titanium dioxide in order to stick the fine powder to the tip portion; and a membrane molding process to mold the tip portion having the fine powder sticking thereto in the dipping and sticking process into a glass membrane having a predetermined shape.

The responsive glass membrane for the ion electrode according to the present invention also can be produced by way of the following processes: a solution yielding process, wherein titanium alkoxide is hydrolyzed in a solvent, while being thermally decomposed at a predetermined temperature to yield a coating solution; a coating process to coat the glass membrane surface with the coating solution; and a pore forming process to form a pore for imparting ion conductivity.

Methods for applying the coating solution on the glass membrane surface during the coating process include a dip coating method, a spin coating method, a thermal spraying method, and a power jet method.

As the method for controlling the porosity of the glass membrane during the pore forming process, it is contemplated that the coating solution includes, for example, polyvinylpyrrolidone, polyethyleneglycol, or polyvinyl alcohol.

Material glass of the responsive glass membrane for the ion electrode has an expansion coefficient proximate to that of titanium dioxide. Therefore, when the microparticle of titanium dioxide sticks to the glass membrane kept molten, the titanium dioxide can be kept bonded without coming unstuck from the glass membrane even after the glass has cooled.

Effect of the Invention

As described above, according to the present invention, a slight increase of the hydrophilicity of titanium dioxide makes the sensitive glass hardly stained at the time of measuring the ion such as pH under natural light or normal indoor lighting, while causing no potential variation that affects the ion measurement such as pH measurement, and no oxidation action is developed which decomposes and alters an ingredient of the test solution. On the other hand, the ultraviolet irradiation at the time of cleaning induces the photocatalytic function derived from titanium dioxide, so that a self-cleaning function can be fulfilled. As such, an accurate measurement of the ion such as pH can be performed without affecting the test solution to be measured, and an ion electrode can be cleaned easily, thereby enabling a stable and highly-accurate measurement to be performed with fewer residues of stains and the affection thereby. Moreover, the number of cleanings using a detergent can be reduced compared to the conventional ion electrode, so that the number of the compensations of the ion concentration also can be reduced.

DESCRIPTION OF REFERENCE NUMERALS

Figure 1:
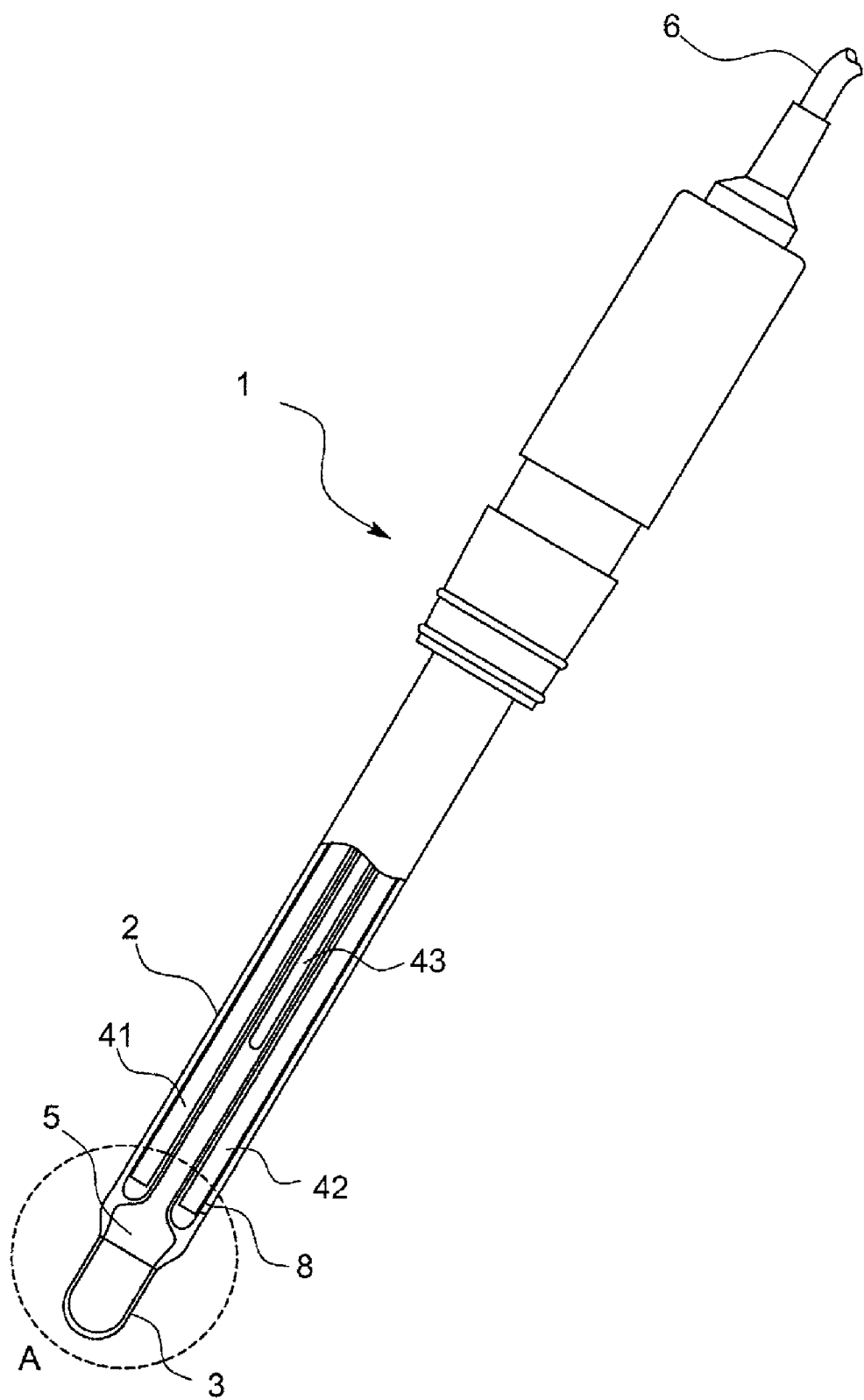
FIG. 1 is a partial cutaway view showing a part of the inner structure of a glass electrode according to an embodiment of the present invention.

1 . . . . Glass electrode
2 . . . . Support tube
3 . . . . Sensitive glass membrane
4 . . . . Internal electrode
5 . . . . Internal liquid
6 . . . . Lead
7 . . . . Microparticle

PREFERRED EMBODIMENTS OF THE INVENTION

A glass electrode as a pH electrode according to an embodiment of the present invention will described below referring to the drawings.

Figure 2:
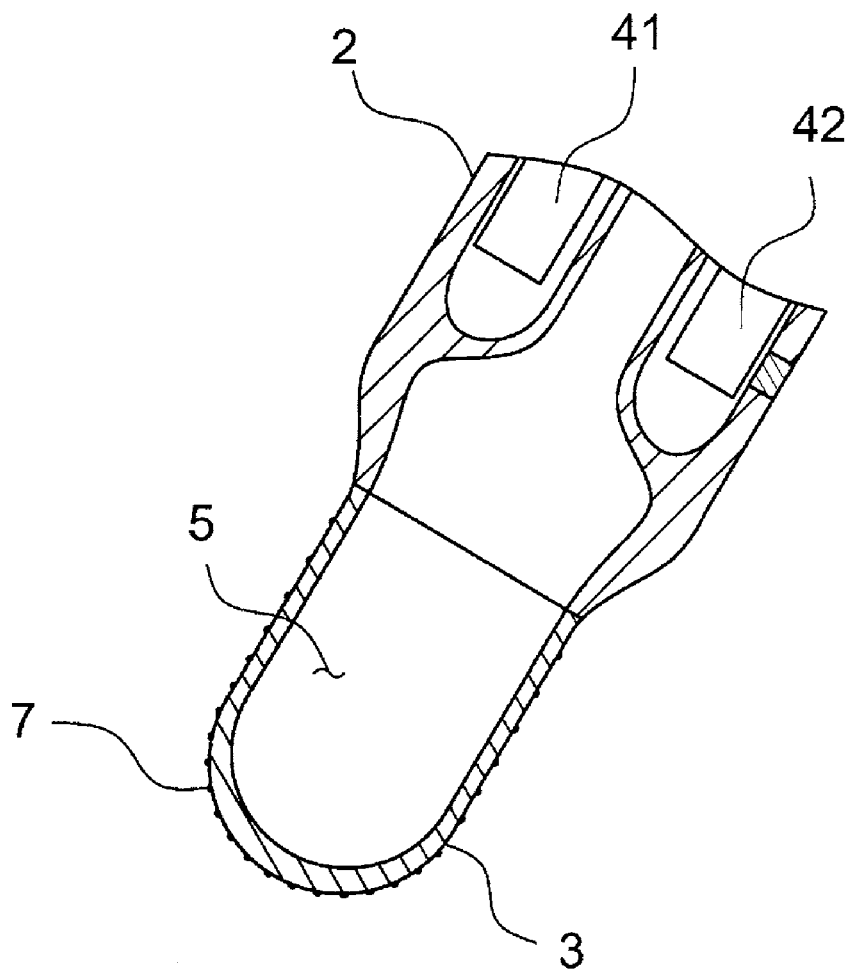
FIG. 2 is an enlarged view of the proximity of the responsive glass membrane 3, (A), in FIG. 1.

As shown in FIGS. 1 and 2, a glass electrode 1 according to the present invention is provided with a cylindrical support tube 2 made of glass, and a responsive glass membrane 3 joined to the tip of the support tube 2.

The support tube 2 accommodates internal electrodes 41, 42, and 43, and is filled with an internal liquid 5. A lead 6 is connected to an internal electrode 4, and extends from a base end of the support tube 2 to the outside to connect to a pH meter body (not shown).

It is necessary for the responsive glass membrane 3 to be made using multicomponent glass with high lithium (Li) content as the material thereof to generate sufficient electromotive force; for example, lithium is added to silicate glass, phosphate glass, and borate glass to make a mixture to be used as a material glass. In order to join the responsive glass membrane 3 to the support tube 2, for example, the following procedures are taken: the material glass used for the responsive glass membrane 3 is kept molten in a furnace maintained at a thousand and several hundred degrees; and the tip portion of the support tube 2 is soaked therein and then raised at a predetermined speed. Then, blow molding enables the tip portion of the responsive glass membrane 3 to take the form of approximately hemispherical shape.

A microparticle 7 comprising rutile-type titanium dioxide or a microparticle 7 comprising amorphous titanium dioxide (illustrated in exaggerated form for understanding) stick to the approximately hemispherical-shaped tip portion of the responsive glass membrane 3. In order to stick the microparticle 7 comprising the rutile-type titanium dioxide or the microparticle 7 comprising the amorphous titanium dioxide to the approximately hemispherical-shaped tip portion of the responsive glass membrane 3, the glass raw material of the responsive glass membrane 3 is melted and subjected to blow molding to form the tip portion into approximately hemispherical shape, while the microparticle 7 is suspended in the air by supplying airflow to the microparticle 7 by a fan, shaking the container that includes the microparticle 7, or discharging the microparticle 7 along with the air compressed by a compressor. The blow-molded tip portion of the responsive glass membrane 3 kept molten is brought closer to such air, thereby sticking the microparticle 7 to the glass membrane surface kept molten.

For example, the microparticle 7 to be stuck has the diameter preferably from 1 to 100 nm, and more preferably from 10 to 50 nm. More specifically, the microparticle is preferably a nanoparticle.

The microparticle 7 comprising the rutile-type titanium dioxide not only comprises the rutile-type titanium dioxide, but can include other ingredients as long as those do not affect the photocatalytic function.

The light intensity of the ultraviolet irradiation at the level of inducing the photocatalytic function of anatase titanium dioxide applies the rutile-type titanium dioxide and the amorphous titanium dioxide sticking to the glass membrane surface of the responsive glass membrane 3 a slight hydrophilicity, but does not induce an oxidation action. Therefore, using the glass electrode 1 for the pH measurement of a test solution under normal laboratory lighting or natural outdoor light makes the responsive glass membrane 3 hardly stained, while generating no potential variation that affect the pH measurement and no decomposition/alternation of the ingredients of the test solution, thereby enabling pH to be measured accurately. However, the ultraviolet irradiation using an LED, a hydrogen lamp, a xenon discharge tube, a mercury lamp, a ruby laser, a YAG laser, an excimer laser, or a dye laser as a light source induces the photocatalytic function of titanium dioxide, so that a self-cleaning function is fulfilled in which a stuck organic substance is decomposed by the oxidation action, and a superhydrophilic action makes the stuck substance easy to remove.

Figure 3:
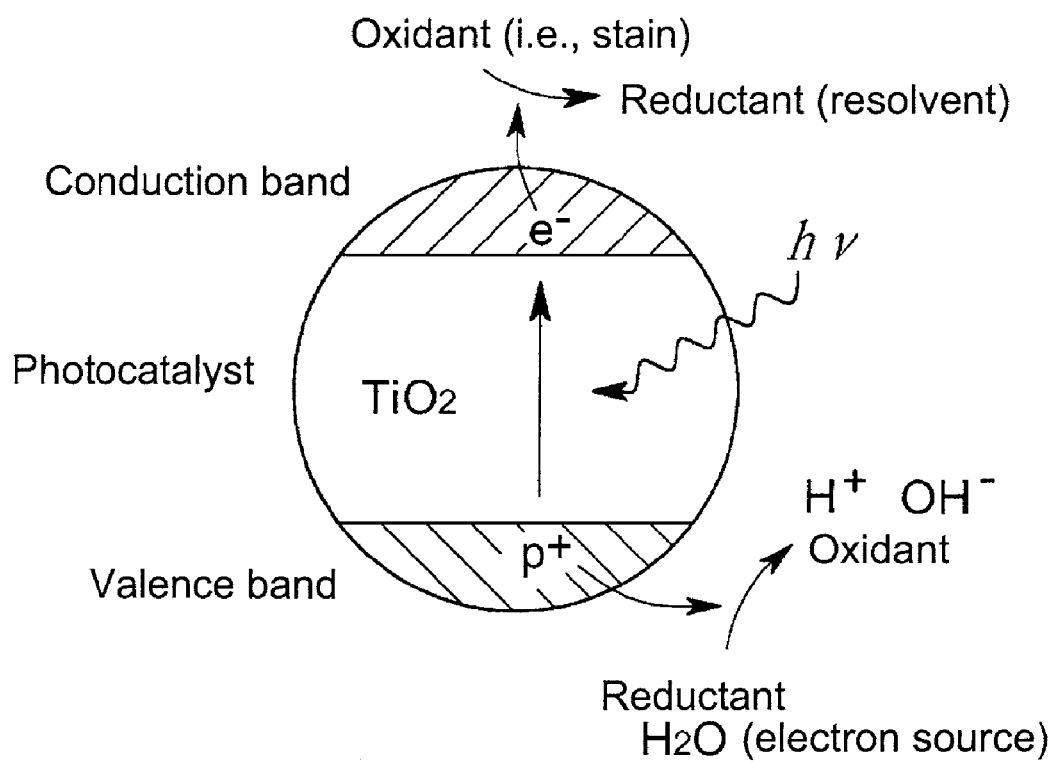
FIG. 3 is a conceptual diagram of an oxidation action due to a photocatalytic function.
Figure 4:
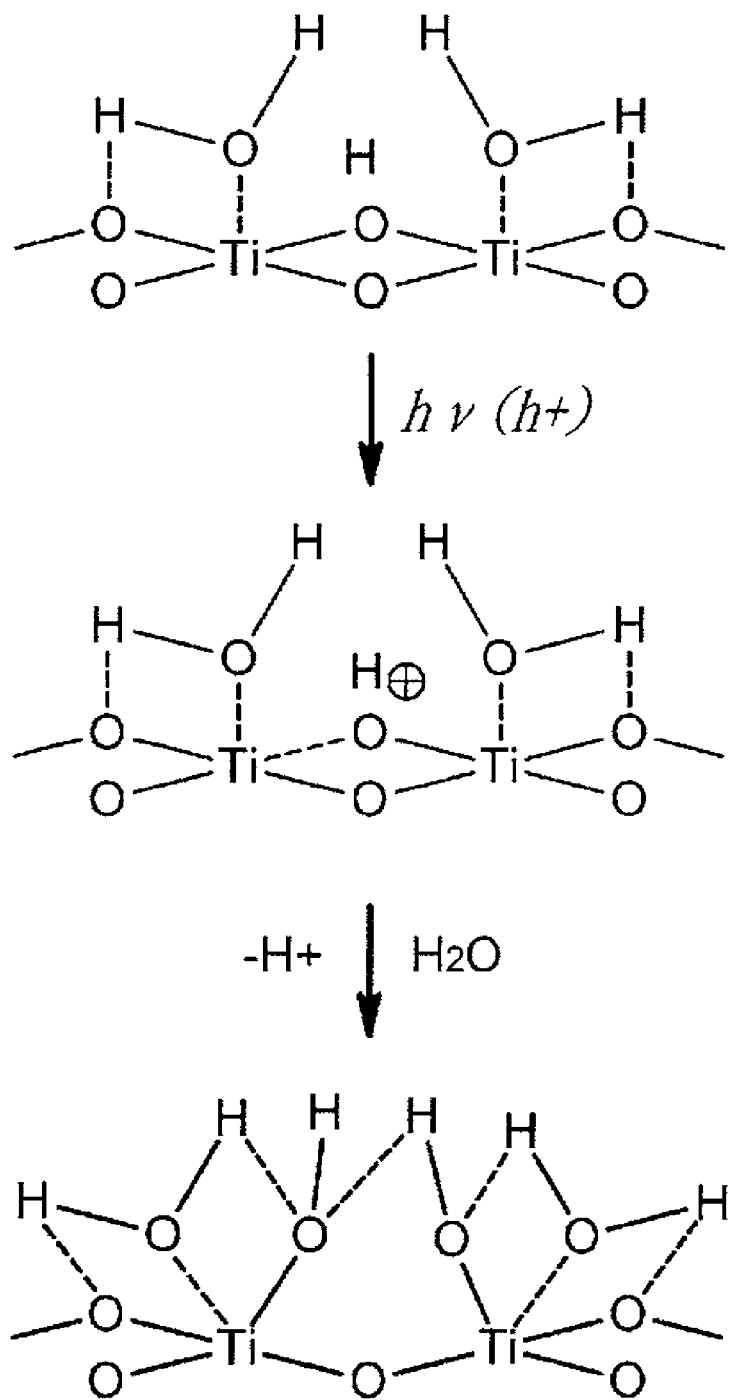
FIG. 4 is a conceptual diagram of a superhydrophilic action due to the photocatalytic function.

The concept of oxidation/reduction action by the photocatalytic function of titanium dioxide (semiconductor) as mentioned above is shown in FIG. 3. When the light having energy higher than the band gap is irradiated, it is absorbed to excite an electron in a valence band to the conduction band, as well as a positive hole is generated in the valence band. The excited electron moves to the chemical substance outside of the photocatalyst, and then the chemical substance is reduced. Then, the movement of the positive hole causes the oxidation. In addition, the concept of a superhydrophilicity action is shown in FIG. 4. It is considered that the reaction by the positive hole yields a relatively instable hydrophilic radical on a surface of titanium oxide, which offers the hydrophilicity. Note that the light irradiation also increases the hardness of titanium dioxide.

A silver chloride electrode, for example, is used as the internal electrode 4, and a potassium chloride solution whose pH is controlled to 7, for example, is used as the internal liquid 5.

When pH of the test solution is measured using the glass electrode 1, soaking the responsive glass membrane 3 of the glass electrode 1 in the test solution whose pH is desired to be measured generates the electromotive force on the responsive glass membrane 3 corresponding to a difference of pHs between the internal liquid 5 and the test solution. The electromotive force is measured as the potential difference (voltage) between the internal electrode 4 of the glass electrode 1 and an internal electrode of a reference electrode by using the reference electrode (not shown) to determine the pH. Since the electromotive force varies depending on the temperature, it is preferable that a temperature element is used to correct the aforementioned potential difference using the output signal value thereof as a parameter so as to determine the pH of the test solution, and then provide a readout on a pH meter body.

Note that the present invention is not limited to the embodiments described above.

For example, although the embodiment described above takes the method of production of the responsive glass membrane in which the suspended microparticle sticks to the glass membrane surface kept molten, the production can be performed by the other methods as follows.

Specifically, the responsive glass membrane also can be manufactured by the following processes: a melting process to melt the tip portion of the glass tube; a dipping and sticking process to dip the tip portion molten during the melting process into a mounted aggregation of fine powder of titanium dioxide to stick the fine powder to the tip portion; and a membrane molding process to mold the tip portion to which the fine powder sticks during the dipping and sticking process into a glass membrane having a predetermined shape, wherein the rutile-type or amorphous-type titanium dioxide is bonded on the glass surface.

More specifically, the molding can be performed by dipping the glass tube having an end portion that is melted and closed into the aggregation of the microparticles, for example, heaped on a flat plate or included in a container to stick the microparticle to the tip portion, and then supplying an air from the other end portion to expand the aforementioned end portion.

Such method does not require a suspension device, as compared to the embodiments described above, and it is only necessary to mount the aggregation of the microparticles on a surface or included in the container. Therefore, the responsive glass membrane can be manufactured easily and readily.

Furthermore, the responsive glass membrane also can be molded by the so-called sol-gel method. The production can be performed by the following processes: a solution yielding process, wherein titanium alkoxide is hydrolyzed in a solvent, while being thermally decomposed at a predetermined temperature to yield a coating solution; a coating process to coat the glass membrane surface with the coating solution; and a pore forming process to form a pore for imparting ion conductivity.

More specifically, titanium alkoxide such as titanium tetraisopropoxide is hydrolyzed in a solvent such as alcohol, while being thermally decomposed at a predetermined temperature to yield a coating solution (the solution yielding process). Then, the coating solution is applied on the glass membrane surface by the dip-coating method (the coating process). Here, it is effective for controlling the porosity of the membrane to allow the coating solution to include, for example, polyvinylpyrrolidone, polyethyleneglycol, or polyvinyl alcohol. Next, the coating solution is applied on the glass membrane surface, which then undergoes a thermal treatment and is decomposed to form a pore for imparting the ion conductivity (the pore forming process).

The pH electrode of the present invention is not limited to the glass electrode, and may encompass a combined electrode, in which the glass electrode and the reference electrode are combined, or a one-piece electrode, in which a temperature compensation electrode is also integrated into the combined electrode.

The tip portion of the responsive glass membrane is not limited to the approximately hemispherical shape, and may be formed in any shape as long as the pH measurement function can be fully fulfilled.

The ultraviolet light source may be provided apart from the pH electrode of the present invention, while the pH electrode of the present invention itself may be provided with the ultraviolet light source.

The pH measurement device may be structured by the combination of the glass electrode, the reference electrode, the pH meter itself, and the ultraviolet light source.

A pinhole opened at the tip portion of the responsive glass membrane can be used as a liquid junction of the reference electrode.

In the aforementioned embodiments, the microparticle 7 comprising the rutile-type titanium dioxide or the microparticle 7 comprising the amorphous titanium dioxide stick to the tip portion of the responsive glass membrane, whereas the same effect can be obtained by sticking the brookite-type titanium dioxide.

An appropriate change of the glass raw material of the responsive glass membrane makes it possible to configure an ion-selective electrode (ion electrode) having the ion selectivity, other than the pH electrode. The ion-selective electrode (ion electrode) is deemed to include a chloride ion-selective electrode, a potassium ion-selective electrode, a nitrate ion-selective electrode, a sodium ion-selective electrode, a thiocyanate ion-selective electrode, and a copper ion-selective electrode.

In addition, it will, of course, be appreciated that various modifications can be made without departing from the spirit and scope of the invention.

INDUSTRIAL APPLICABILITY

According to the present invention, it is possible to prevent the pH electrode from being stained and to clean the pH electrode easily without affecting the test solution to be measured. Therefore, a stable and highly-accurate measurement can be performed with fewer residues of stains and the affection thereby.

What is claimed is:

1. A method of production of a responsive glass membrane for an ion electrode, comprising:
    a membrane molding process to melt a glass raw material and mold it into a glass membrane having a predetermined shape; and
    a sticking process to stick titanium dioxide to a surface of the glass membrane kept molten at intervals.

2. A responsive glass membrane for an ion electrode achieved by the production method according to claim 1.

3. A method of production of a responsive glass membrane for an ion electrode, comprising:
    a membrane molding process to melt a glass raw material and mold it into a glass membrane having a predetermined shape; and
    a sticking process to stick a microparticle comprising titanium dioxide to a surface of the glass membrane kept molten.

4. The method of production of the responsive glass membrane for the ion electrode according to claim 3, further comprising:
    a suspending process to suspend the microparticle within gas, wherein:
    the microparticle suspended within the gas sticks to the glass membrane surface in the sticking process.

5. A method of production of a responsive glass membrane for an ion electrode, comprising:
    a melting process to melt a tip portion of a glass tube;
    a dipping and sticking process to dip the tip portion melted during the melting process into a mounted aggregation of fine powder of titanium dioxide to stick the fine powder to the tip portion; and
    a membrane molding process to mold the tip portion having the fine powder sticking thereto in the dipping and sticking process into a glass membrane having a predetermined shape.

6. A method of production of a responsive glass membrane for an ion electrode, comprising:
    a solution yielding process, wherein titanium alkoxide is hydrolyzed in a solvent, while being thermally decomposed at a predetermined temperature to yield a coating solution;
    a coating process to coat a glass membrane surface with the coating solution; and
    a pore forming process to form a pore for imparting ion conductivity.

7. A responsive glass membrane for an ion electrode, wherein a microparticle comprising rutile-type or brookite-type titanium dioxide or a microparticle comprising amorphous titanium dioxide sticks directly to a glass membrane surface.

8. An ion electrode, comprising a responsive glass membrane including a microparticle comprising rutile-type or brookite-type titanium dioxide or a microparticle comprising amorphous titanium dioxide sticking directly to the surface thereof.

* * * * *